United States Patent
Koehler et al.

(10) Patent No.: US 9,625,546 B2
(45) Date of Patent: Apr. 18, 2017

(54) METHOD AND MAGNETIC RESONANCE SYSTEM TO ACQUIRE MR DATA AND TO DETERMINE A B1 MAGNETIC FIELD

(71) Applicants: Michael Koehler, Nuermberg (DE); Thorsten Speckner, Erlangen (DE)

(72) Inventors: Michael Koehler, Nuermberg (DE); Thorsten Speckner, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 618 days.

(21) Appl. No.: 14/169,556

(22) Filed: Jan. 31, 2014

(65) Prior Publication Data

US 2014/0218021 A1  Aug. 7, 2014

(30) Foreign Application Priority Data

Feb. 1, 2013  (DE) .................. 10 2013 201 670

(51) Int. Cl.
*G01R 33/44* (2006.01)
*G01R 33/24* (2006.01)
(Continued)

(52) U.S. Cl.
CPC ......... *G01R 33/443* (2013.01); *G01R 33/246* (2013.01); *G01R 33/54* (2013.01); *A61B 5/055* (2013.01)

(58) Field of Classification Search
CPC .... G01R 33/443; G01R 33/246; G01R 33/54; A61B 5/055
See application file for complete search history.

(56) References Cited

U.S. PATENT DOCUMENTS 5,247,255 A  9/1993  McKinnon et al.
5,379,766 A *  1/1995  McKinnon ......... G01R 33/5673
                                                      324/309
(Continued)

FOREIGN PATENT DOCUMENTS

JP  H03106339 A  5/1991
WO  2012140536 A1  10/2012

OTHER PUBLICATIONS

"DREAM—A Novel Approach for Robust, Ultrafast, Multislice B1 Mapping," Nehrke et al., Magnetic Resonance in Medicine, vol. 68 (2012), pp. 1517-1526.
(Continued)

*Primary Examiner* — Rodney Bonnette
(74) *Attorney, Agent, or Firm* — Schiff Hardin LLP (57) ABSTRACT

In a method to acquire magnetic resonance (MR) data within a volume segment with a magnetic resonance system, the MR data are repeatedly acquired with a sequence that includes radiating a first resonant RF pulse, radiating a second resonant RF pulse, applying a dephasing first gradient after the first resonant RF pulse and before the second resonant RF pulse, radiating a third resonant RF pulse after the second resonant RF pulse, applying a second gradient after the third RF pulse in order to refocus a stimulated echo of a magnetization component prepared by the first gradient, and read out MR data. At least one of the first gradient and/or the second gradient is/are different in a respective repetition of the sequence and an additional repetition of the sequence that directly follows the respective repetition.

15 Claims, 4 Drawing Sheets

(51) Int. Cl.
*G01R 33/54* (2006.01)
*A61B 5/055* (2006.01)

(56) References Cited

U.S. PATENT DOCUMENTS

| | | |
|---|---|---|
| 6,127,825 A | 10/2000 | Goto |
| 8,198,891 B2 | 6/2012 | Sacolick et al. |
| 2002/0050816 A1 | 5/2002 | Miyoshi |
| 2003/0160616 A1 | 8/2003 | Asano et al. |
| 2003/0218459 A1 | 11/2003 | Reddy et al. |
| 2004/0164737 A1 | 8/2004 | Feiweier |
| 2010/0315084 A1 | 12/2010 | Sacolick et al. |
| 2012/0249138 A1 | 10/2012 | Pfeuffer |
| 2014/0218022 A1* | 8/2014 | Koehler ............... G01R 33/246 324/301 |

OTHER PUBLICATIONS

"Handbook of MRI Pulse Sequences," Bernstein et al., (2004), pp. 266-267 and 350-351.

"B1 Mapping by Bloch-Siegert Shift," Sacolick et al., Magnetic Resonance in Medicine, vol. 63 (2010), pp. 1315-1322.

"Fast B1 Mapping using a Steam-based Bloch-Siegert Preparation Pulse," Nehrke et al., Proc. Intl. Soc. Mag. Reson. Med., vol. 19 (2011), p. 4411.

* cited by examiner

METHOD AND MAGNETIC RESONANCE SYSTEM TO ACQUIRE MR DATA AND TO DETERMINE A B1 MAGNETIC FIELD

BACKGROUND OF THE INVENTION

Field of the Invention

The present invention concerns a method in order to acquire MR data (for example to create MR images) as well as a method in order to determine a B1 magnetic field. Moreover, the present invention concerns a magnetic resonance system designed in order to implement one or both of such methods.

Description of the Prior Art

The precise knowledge of the B1 magnetic fields present in the examined region of the examination subject is of great importance for many applications in the field of magnetic resonance tomography, for example for the calculation of an RF pulse in multichannel transmission operation or for quantitative T1 examinations. In a high, static B0 magnetic field (for example of a strength of 3 Tesla or more), distinctive spatially dependent variations of the B1 magnetic field can occur due to subject-specific variations of the conductivity and susceptibility. Therefore, a subject-specific determination of the actual B1 magnetic field that is present is indispensable for many applications given a defined, set transmission power.

One possibility to determine the actual B1 magnetic field is offered by what is known as the Bloch-Siegert method, as described in DE 102010017315A1 and in "B1 mapping by Bloch-Siegert shift", L. Sacolick et al., Magn. Reson. Med. 2010; 63: Pages 1315-1322. A phase shift of the nuclear spins is thereby measured, which is generated by a non-resonant RF pulse. The B1 amplitude of the B1 magnetic field generated by the non-resonant RF pulse can be calculated using the magnitude of the phase shift.

An accelerated method to determine the actual B1 magnetic field is described in "Fast B1 Mapping using a STEAM-based Bloch-Siegert Preparation", K. Nehrke et al., Proc. Intl. Soc. Mag. Reson. Med. 19 (2011); Page 4411.

In other known MR methods with which MR images are generated, for example, a stimulated echo is generated which is detected upon readout of the MR data. The problem can occur that a magnetization prepared in a previous sequence negatively affects or adulterates the MR data acquired for the current sequence. For example, artifacts can occur in an MR image reconstructed from the MR data. If such an MR method based on the stimulated echo is used to determine the B1 magnetic field, a phase shift, and therefore the B1 magnetic field amplitude, are disadvantageously determined incorrectly due to this problem.

SUMMARY OF THE INVENTION

An object of the present invention is to at least alleviate these problems for general MR methods based on the stimulated echo, and in particular for methods to determine a B1 magnetic field.

Within the scope of the present invention, a method is provided to acquire MR data within a volume segment with a magnetic resonance system. This method repeatedly applies a sequence to a subject to acquire the MR data therefrom. This sequence includes the following steps.

A first resonant RF pulse is radiated, followed by radiation of a second resonant RF pulse. A dephasing first magnetic field gradient is applied after the first resonant RF pulse and before the second resonant RF pulse. A third resonant RF pulse is radiated after the second resonant RF pulse. A second magnetic field gradient is applied after the third RF pulse in order to refocus a stimulated echo of a magnetization component prepared by the first gradient. This second magnetic field gradient is adapted to the first magnetic field gradient so that the polarity of both magnetic field gradients is the same, for example. The MR data are read out. In the repetitions of this sequence, a dissimilarity is intentionally produced between a respective sequence repetition and a next-successive sequence repetition that this dissimilarity is (i) directly chronologically follows the respective sequence repetition. The first gradient of the next-successive sequence differs from the first gradient of the respective sequence, or (ii) the second gradient of the next-successive sequence differs from the second gradient of the respective sequence, or (iii) both (i) and (ii). If both the first and second gradient are modified, a difference moment by which the gradient moment or the first gradient of the respective sequence differs from the gradient moment or the first gradient of the next-successive sequence is preferably equal to a difference moment by which the gradient moment of the second gradient of the respective sequence differs from the gradient moment generated by the second gradient of the next-successive sequence.

As is known, the gradient moment of a gradient pulse is the area under the curve that represents the gradient pulse, i.e. the time integral of the gradient pulse.

A resonant RF pulse has a flip angle by which the RF pulse deflects or flips nuclear spins that have essentially the same frequency as the RF pulse. In contrast to this, a non-resonant RF pulse has no flip angle, such that the non-resonant RF pulse does not affect the angle of the nuclear spins relative to the direction of the basic magnetic field.

As used herein, and as is commonly understood, an application of a magnetic field gradient is the application of a corresponding magnetic field gradient moment. A gradient or a gradient moment can have components in one, two or in all three spatial directions. Expressed differently, both the first and second gradients can be effective on any or all spatial axes. Moreover, both the first gradient moment (i.e. the gradient moment of the first gradient) and the second gradient moment (i.e. the gradient moment of the second gradient) can be added to gradient moments that are components of the sequence for other reasons.

Because the first gradient (or the first gradient moment) and/or the second gradient (or the second gradient moment) is/are set differently in successive sequence repetitions or MR data acquisitions, advantageously only the echo of that (longitudinal) magnetization component, which was also prepared in the same sequence repetition or acquisition (via the first gradient moment) is refocused in the readout of the MR data. (Longitudinal) magnetization components of preceding sequences have different dephasings and are advantageously not refocused upon readout of the current sequence repetition. In other words, at the point in time of the readout of the current sequence repetition, only the stimulated echo is acquired that originates from the (longitudinal) magnetization component that was prepared in the associated preparation portion of that sequence repetition. An adulteration of the measured MR data is therefore prevented or at least reduced, so image artifacts in the MR images created from the MR data are advantageously likewise at least reduced.

So that only the stimulated echo that originates from that magnetization component that was prepared during the current sequence repetition is detected at the point in time of the readout of the current sequence repetition, the first gradient or the first gradient moment and the second gradient or the second gradient moment must be adapted to one another, or have a defined relationship. It is normally the case that an increase (or reduction) of the first gradient moment by a determined percentile leads to an increase (or reduction) of the second gradient moment by the same percentile. The relationship between the two gradient moments is dependent on the temporal length of the readout of the MR data, for example.

According to the invention, the volume segment in which the B1 magnetic field should be determined can include a slice or comprise a slice. In this case, a respective slice selection gradient is applied during the first resonant RF pulse, during the second resonant RF pulse and during the third resonant RF pulse, such that the resonant RFD pulses essentially affect only the nuclear spins of the slice.

However, according to the invention it is also possible that the first, second and third resonant RF pulse respectively excite a three-dimensional volume segment.

In other words: the present invention is usable both in two-dimensional (slice) acquisition of the MR data, and in three-dimensional acquisition of the MR data.

According to a preferred embodiment according to the invention, after the second resonant RF pulse and before the third resonant RF pulse, a spoiler gradient is applied with which transverse components of the magnetization are dephased.

The transverse components of the magnetization can advantageously be so strongly dephased by the spoiler gradient (or by the spoiler gradient moment) that these magnetization components no longer have any significant contribution to the signal or to the result upon readout of the MR data.

The first and the second resonant RF pulses can each have a flip angle of 90°.

By the use of a first resonant RF pulse with a flip angle of 90°, the magnetization is deflected optimally strongly (in comparison to other flip angles) in the transverse plane (orthogonal to the longitudinal direction). A second resonant RF pulse with a flip angle of 90° similarly ensures that the magnetization is flipped again in the longitudinal direction. If the flip angle of the first resonant RF pulse is 90°, a maximum portion of the original magnetization is deflected in the transverse plane and can be dephased with the first gradient. If the second resonant RF pulse has a flip angle of 90°, the entire magnetization that was dephased or prepared by the first gradient is converted into the longitudinal magnetization component (and is essentially remains there until it is converted again into transverse magnetization by the third resonant RF pulse).

However, a flip angle of precisely 90° cannot always be achieved, for example due to inhomogeneities. Therefore, the present invention does not preclude that the first and second resonant RF pulses have a flip angle that deviates slightly from 90° by an amount within a tolerance range.

If the two resonant RF pulses have a flip angle differing from 90°, a defined proportion of the magnetization component present before the radiation of the respective resonant RF pulse remains. The greater the deviation of the actual flip angle of the first or the second resonant RF pulse from 90°, the more that a magnetization prepared in the previous sequence repetition influences the stimulated echo of the current sequence repetition. In other words the advantageous effect of present invention become more important the greater the deviation of the actual flip angle from 90°.

In particular, the radiation of the third resonant RF pulse, the application of the second magnetic field gradient, and the readout are implemented multiple times.

The entirety of k-space (or at least a portion of k-space) is preferably scanned by the aforementioned steps being executed multiple times. The MR data (amplitude and phase) for arbitrary points of the volume segment are thereby determined.

According to the invention, it is also possible to radiate an additional (final) resonant RF pulse with a relatively large flip angle (80°-90°) at the end of the sequence—after the (last) readout of the MR data—and to subsequently apply an additional spoiler gradient. The additional resonant RF pulse converts longitudinal magnetization into transverse magnetization, which is then subsequently dephased by the additional spoiler gradient, so that it no longer contributes to a measurement signal in the following sequence repetition.

The present invention also encompasses a method to determine a B1 magnetic field within a volume segment with a magnetic resonance system. The method according to the invention for the determination of the B1 magnetic field uses the above-described method according to the invention for the acquisition of MR data in order to detect phase shift of a rotation movement of nuclear spins which is generated by radiation of a non-resonant RF pulse. In the method to determine the B1 magnetic field, a processor determines an amplitude of the B1 magnetic field depending on this phase shift. For this purpose, the non-resonant RF pulse is radiated after the first resonant pulse and before the second resonant RF pulse. The non-resonant RF pulse is therefore radiated either before the first gradient or after the first gradient. The non-resonant RF pulse is radiated during the determined sequence and/or during the additional sequence.

The method according to the invention for the determination of the B1 magnetic field includes three variants:

The non-resonant RF pulse is radiated both during the respective sequence and during the next-successive sequence.

The non-resonant RF pulse is radiated only during the respective sequence but not during the next-successive sequence.

The non-resonant RF pulse is not radiated during the respective sequence but is radiated during the next-successive sequence.

If the non-resonant RF pulse is radiated both during the respective sequence and during the next-successive sequence, the non-resonant RF pulse advantageously has a first frequency in the respective sequence and a second frequency in the next-successive sequence, the second frequency differing from the first frequency.

The phase shift is calculated using a difference of a phase value which is determined using the MR data detected during the respective sequence, with a phase value which is determined using the MR data detected during the next-successive sequence. In other words: the phase shift depending on which the actual B1 magnetic field is determined is determined using a difference of two phase values which are detected during the respective sequence and the next-successive sequence.

The B1 magnetic field can then be determined depending on this phase shift $\phi$ via the following Equation (1).

$$\phi = \int_0^T \frac{(\gamma B_1(t))^2}{2\omega_{HF}(t)} dt \qquad (1)$$

Wherein $\omega_{RF}$ is what is known as the off-angular frequency, i.e. the difference between the system angular frequency and the angular frequency of the non-resonant RF pulse, γ is the gyromagnetic ratio, T is the entire pulse duration of the non-resonant RF pulse which, for example, is in a range from 4 to 8 ms.

It is noted that $B_1(t)$ corresponds to the time curve of the B1 magnetic field, which (except for the amplitude) is assumed to be known since the pulse shape of the non-resonant RF pulse that is executed is known. The B1 amplitude can be determined using Equation (1) described above via the knowledge of the time curve.

According to a preferred embodiment according to the invention, the frequency of the non-resonant RF pulse in two successive sequences is situated once above and the other time below the system frequency.

For example, the frequency f of the non-resonant RF pulse in a first (or second) sequence can be determined according to the following Equation (2), and the frequency f of the non-resonant RF pulse in a second (or first) sequence can be determined according to the following Equation (3), wherein it is assumed that the second sequence is introduced directly after the first sequence.

$$f=f_{sys}+f_{RF} \quad (2)$$

$$f=f_{Sys}-f_{RF} \quad (3)$$

Wherein $f_{Sys}$ is the system frequency, and $f_{RF}$ is the difference of the frequency f of the non-resonant RF pulse from the system frequency (thus the off-frequency). For example, the off-frequency $f_{RF}$ can be in a range from 2000 to 8000 Hz.

According to a preferred embodiment according to the invention, the sequence is radiated (repeated) three times. The non-resonant RF pulse is not radiated in precisely one of these three sequences, and therefore is radiated in two of these three sequences. In this embodiment, it is also the case that the frequency of the non-resonant RF pulse is set differently in the two sequences in which the non-resonant RF pulse is radiated.

Because the B1 magnetic field is determined with three sequences in which the non-resonant RF pulse is not radiated in a sequence, a systematic error can be better detected than this is the case in other variants according to the invention, in which the B1 magnetic field is determined with only two sequences.

Given a magnetic resonance system with multiple transmission channels or multiple RF transmission antennas, the non-resonant RF pulse is respectively radiated by the same group of transmission channels or RF transmission antennas in two sequences in order to thereby measure or determine the B1 magnetic field generated by this group. The corresponding group can also be formed by only one transmission channel or by only one RF transmission antenna.

With this procedure it is advantageously possible to determine the B1 magnetic field for an arbitrary configuration of transmission channels (for example individually for each transmission channel or for an arbitrary combination of multiple transmission channels).

For example, the method according to the invention for the determination of the B1 magnetic field—which method respectively includes two sequences in which the frequency of the non-resonant RF pulse is selected once below and once above the system frequency (for example)—can be implemented N times in order to determine the B1 magnetic field for N configurations of the transmission channels. The non-resonant RF pulses are respectively executed only at the transmission channel corresponding to the configuration or at the group of transmission channels corresponding to the configuration.

According to the prior art, in this case the problem solved by the present invention would occur with particular severity since the magnetization prepared by a channel group would affect the measurement of the channel group following this channel group, which would disadvantageously lead to an additional adulteration in the determination of the B1 magnetic field.

Within the scope of the present invention, a magnetic resonance system is provided to acquire MR data within a volume segment. The magnetic resonance system has an MR data acquisition unit that includes a basic field magnet, a gradient field system, at least one RF transmission/reception antenna, at least one reception coil element, and a control device. The control device serves to control the gradient field system and the at least one RF transmission/reception antenna. The control device is designed in order to receive measurement signals that have been detected by the at least one RF transmission/reception antenna or by the at least on reception coil element. The magnetic resonance system (i.e., the control unit) is designed in order to implement or input the following sequence multiple times to acquire the MR data. For this purpose, the control unit operates the MR data acquisition unit in order to radiate first and second resonant RF pulses with the at least one RF antenna, and to apply a dephasing first gradient with the gradient field system after the first resonant RF pulse and before the second resonant RF pulse, and to radiate a third resonant RF pulse with the at least one RF antenna after the second resonant RF pulse, and to apply a second magnetic field gradient after the third RF pulse, with which second magnetic field gradient a stimulated echo of a magnetization component prepared by the first gradient is refocused with the gradient field system, and in order to read out MR data. Moreover, the control unit operates the MR data acquisition unit in order to select the first (or second) gradient in a respective repetition of the sequence differently from the first (or second) gradient in a next-successive repetition of the sequence, that directly follows the first input.

Moreover, the magnetic resonance system can be designed such so as to implement the method to determine the B1 magnetic field. For this purpose, the control unit operates the MR data acquisition unit in order to radiate the non-resonant RF pulse with a first frequency in the respective repetition of the sequence and to radiate the non-resonant RF pulse with a second frequency (which differs from the first frequency) in the next-successive repetition of the sequence. The control unit furthermore operates the MR data acquisition unit in order to determine a phase shift from a difference of two phase values which are determined from the MR data that are acquired in the aforementioned repetitions of the sequence, and in order to then determine the B1 magnetic field depending on the phase shift.

The advantages of the magnetic resonance system according to the invention essentially correspond to the advantages of the method according to the invention that have been described in detail above.

The present invention also encompasses a non-transitory, computer readable data storage medium encoded with programming instructions or commands, which can be loaded into a memory of a programmable control device or a computer of a magnetic resonance system. Any or all embodiments of the method according to the invention that are described above can be executed when the instructions/commands run in the control device. The programming instructions storage on the storage medium may require other program means (for example libraries and auxiliary functions) in order to realize the corresponding embodiments of the method. The programming instructions can be formatted as a source code (C++, for example) that still needs to be compiled and linked or that only needs to be interpreted, or can be formatted as an executable software code that has only to be loaded into the corresponding computer or control device for execution.

The electronically readable data medium can be, for example, a DVD, a magnetic tape or a USB stick on which the electronically readable control information is stored.

Advantageously, systematic errors due to an incomplete T1 relaxation can be significantly reduced by the present invention in the MR data acquisition, and therefore also in the determination of the B1 magnetic field. The present invention enables a reduction of this measurement error without needing to wait for the complete T1 relaxation between successive sequences or, respectively, sequence executions, so the measurement time can be reduced and image artifacts also can be reduced.

The present invention is particularly suitable for diffusion imaging and for determination of the B1 magnetic field. Naturally, the present invention is not limited to this preferred field of application since the present invention can be used for virtually all methods based on the STEAM preparation. STEAM thereby stands for "STimulated Echo Acquisition Mode".

DESCRIPTION OF THE PREFERRED EMBODIMENTS

Figure 1:
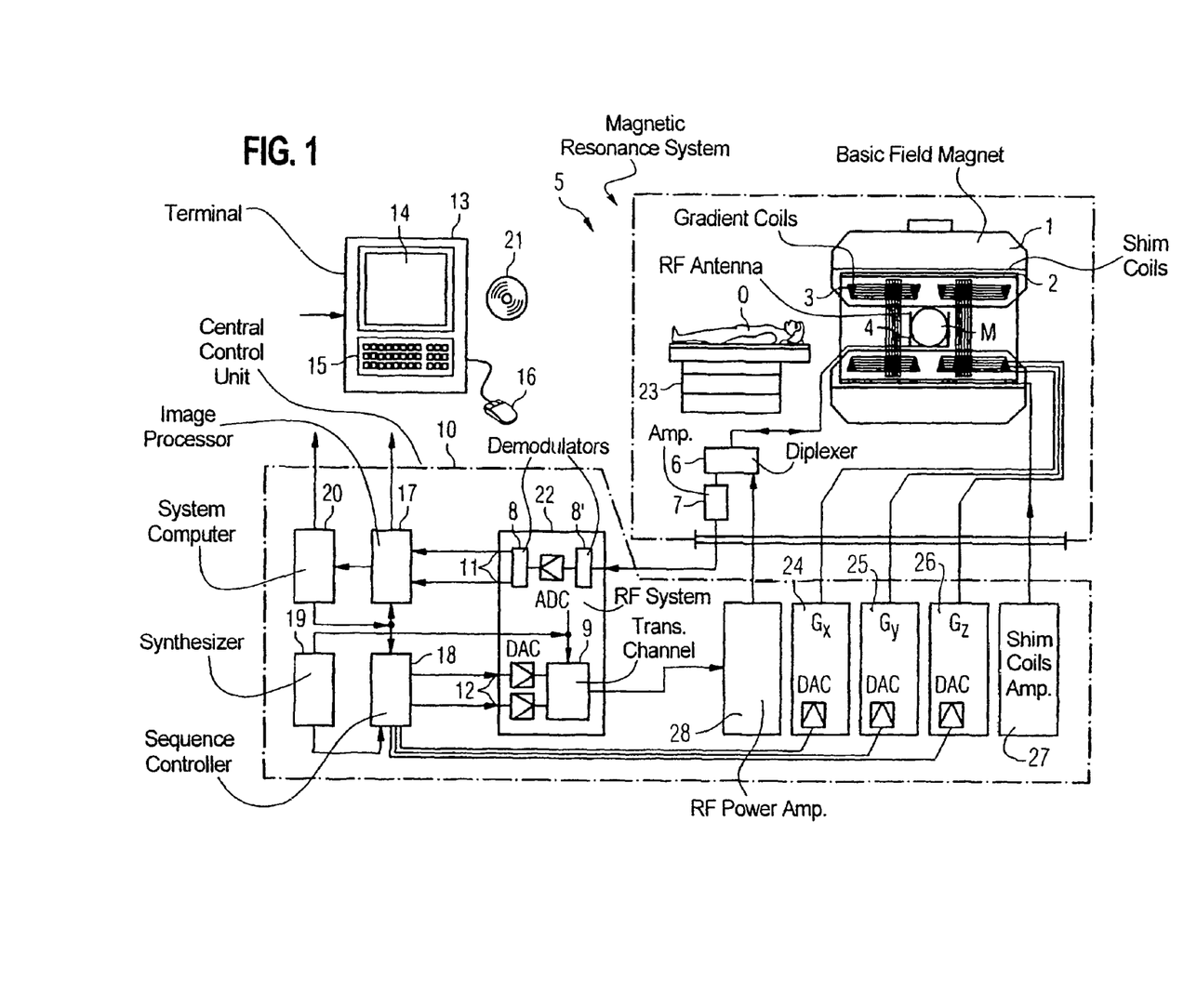
FIG. 1 schematically illustrates a magnetic resonance system according to the invention.

FIG. 1 is a schematic depiction of a magnetic resonance system 5 (magnetic resonance tomography apparatus). A basic field magnet 1 generates a temporally constant, strong magnetic field for polarization or alignment of the nuclear spins in a volume segment of a subject 0 (for example of a part of a human body that is to be examined) which, lying on a table 23, is examined in the magnetic resonance system 5. The high homogeneity of the basic magnetic field that is required for the magnetic resonance measurement is defined in a typically spherical measurement volume M in which the parts of the human body that are to be examined are arranged. To support the homogeneity requirements, and in particular to eliminate temporally invariable influences, what are known as shim plates made of ferromagnetic material are mounted at a suitable location. Temporally variable influences are eliminated by shim coils 2 supplied by a shim coils amplifier 27.

In the basic field magnet 1, a cylindrical gradient field system 3 is used which comprises three sub-windings. Each sub-winding is supplied by a respective amplifier 24, 25 or 26 with current to generate a linear (also temporally variable) gradient field in the respective direction of the Cartesian coordinate system. The first sub-winding of the gradient field system 3 generates a gradient $G_x$ in the x-direction; the second sub-winding generates a gradient $G_y$ in the y-direction; and the third sub-winding generates a gradient $G_z$ in the z-direction. Each amplifier has a digital/analog converter that is controlled by a sequence controller 18 for accurately-timed generation of gradient pulses.

Situated within the gradient field system 3 are one or more radio-frequency antennas 4, which convert the radio-frequency pulses emitted by a radio-frequency power amplifier 28 into an alternating magnetic field for excitation of the nuclei and alignment of the nuclear spins of the subject 0 to be examined, or of the region of the subject 0 that is to be examined, or which also detect an MR signal. Each radio-frequency antenna 4 has one or more RF transmission coils and one or more RF reception coils in the form of an annular (advantageously linear or matrix-like) arrangement of component coils. The alternating field emanating from the precessing nuclear spins—i.e. normally the nuclear spin echo signals caused by a pulse sequence made up of one or more radio-frequency pulses and one or more gradient pulses—is also converted by the RF reception coils of the respective radio-frequency antenna 4 into a voltage (measurement signal) which is supplied via an amplifier 7 to a radio-frequency reception channel 8 of a radio-frequency system 22. The radio-frequency system 22 furthermore comprises a transmission channel 9 in which the radio-frequency pulses are generated for the excitation of magnetic resonance. The respective radio-frequency pulses are digitally represented in the sequence controller 18 as a series of complex numbers based on a pulse sequence predetermined by the system computer 20. This number sequence is supplied as a real part and imaginary part to a digital/analog converter in the radio-frequency system 22 via respective inputs 12, and from the digital/analog converter to a transmission channel 9. In the transmission channel 9, the pulse sequences are modulated on a radio-frequency carrier signal whose base frequency corresponds to the center frequency.

Switching from transmission operation to reception operation takes place via a transmission/reception diplexer 6. The RF transmission coils of the radio-frequency antenna(s) 4 radiate(s) the radio-frequency pulses (resonant and non-resonant) for excitation of the nuclear spins and for generation of the B1 magnetic field into the measurement volume M, and resulting echo signals are scanned via the RF reception coil(s). The correspondingly acquired magnetic resonance signals are phase-sensitively demodulated to an intermediate frequency in a reception channel 8' (first demodulator) of the radio-frequency system 22 and digitized in an analog/digital converter (ADC). This signal is further demodulated to a frequency of 0. The demodulation to a frequency of 0, and the separation into real part and imaginary part, occur in a second demodulator 8 in the digital domain. An MR image or three-dimensional image data set is reconstructed by an image computer 17 from the measurement data acquired in such a manner. The administration of the measurement data, the image data and the control programs takes place via the system computer 20. Based on a specification with control programs, the sequence controller 18 monitors the generation of the respective desired pulse sequences and the corresponding scanning of k-space. In particular, the sequence controller 18 controls the accurately-timed switching of the gradients, the emission of the radio-frequency pulses with defined phase amplitude and the reception of the magnetic resonance signals. The time base for the radio-frequency system 22 and the sequence controller 18 is provided by a synthesizer 19. The selection of corresponding control programs to generate an MR angiography image (which control programs are stored on a DVD 21, for example) and the presentation of the generated MR image take place via a terminal 13, which has a keyboard 15, a mouse 16 and a monitor 14.

Figure 2:
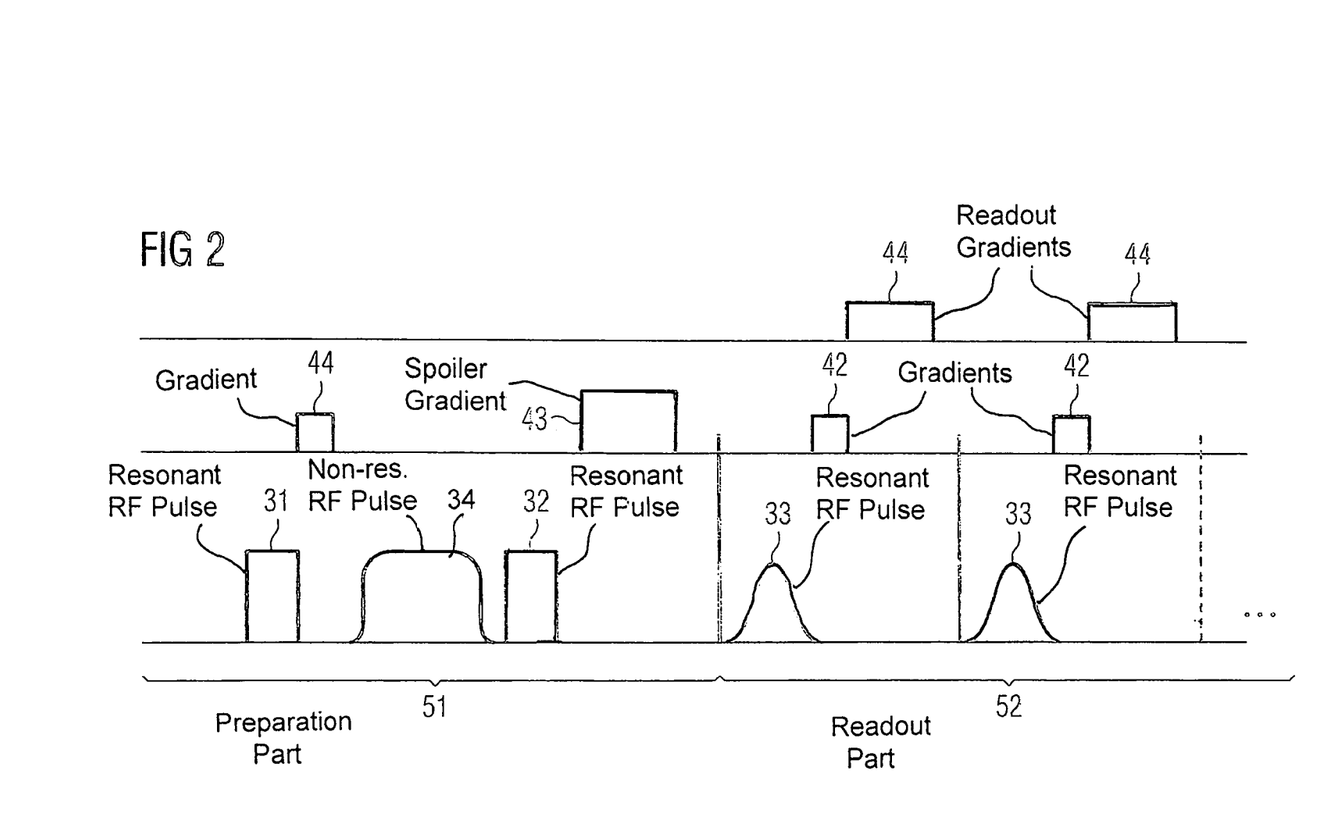
FIG. 2 shows a sequence diagram according to the invention.

The most important components of a sequence according to the invention for the determination of the B1 magnetic field are shown in FIG. 2. Each sequence can thereby be subdivided into a preparation part 51 and a readout part 52.

First, in the preparation part 51 a first resonant RF pulse 31 with a flip angle of at best 90° is radiated, which is followed by a second resonant RF pulse 32 (likewise with a flip angle of at best 90°). The magnetization is dephased between the two resonant RF pulses 31, 32 via application of a first gradient 41 with a first gradient moment. Additionally, a non-resonant RF pulse 34—which generates the B1 magnetic field, and causes a phase shift depending on the strength of the B1 magnetic field that is present at the respective position—is radiated between the two resonant RF pulses 31, 32.

The magnetization present after the second resonant RF pulse 32 is divided up into the following magnetic field components:

An unprepared longitudinal component that corresponds to the unprepared initial magnetization.

A prepared longitudinal component which has been dephased by the selected gradient moment, or by the application of the first gradient 41, and thus has been prepared.

Transverse components.

The relative distribution of the magnetization among these components essentially depends on the deflection angles or, respectively, flip angles which are generated by the two resonant RF pulses 31, 32 in the preparation part 51.

The transverse components of the magnetization can be so strongly dephased by strong spoiler gradients 43 that they essentially no longer contribute to the signal or to the result (readout of the MR data) in the following readout portion 52.

A third resonant RF pulse 33 with a defined flip angle is now radiated to read out the MR data, which is followed by a second rephasing or refocusing gradient 42 with which a defined gradient moment is generated. The MR data are subsequently read out while an additional (readout) gradient 44 is switched.

For example, in order to read out a complete k-space the steps of the radiation of the third resonant RF pulse 33, radiation of the second gradient 42 and readout of the MR data given a switched gradient 44 can be repeated accordingly often before a new sequence repetition is executed with a new preparation part 51.

It is noted that, in addition to the gradients 41-44 shown in FIG. 2, additional gradients (for example phase coding gradients, slice selection gradients or additional spoiler gradients) can be switched in arbitrary directions (for example for flux compensation).

Figure 3:
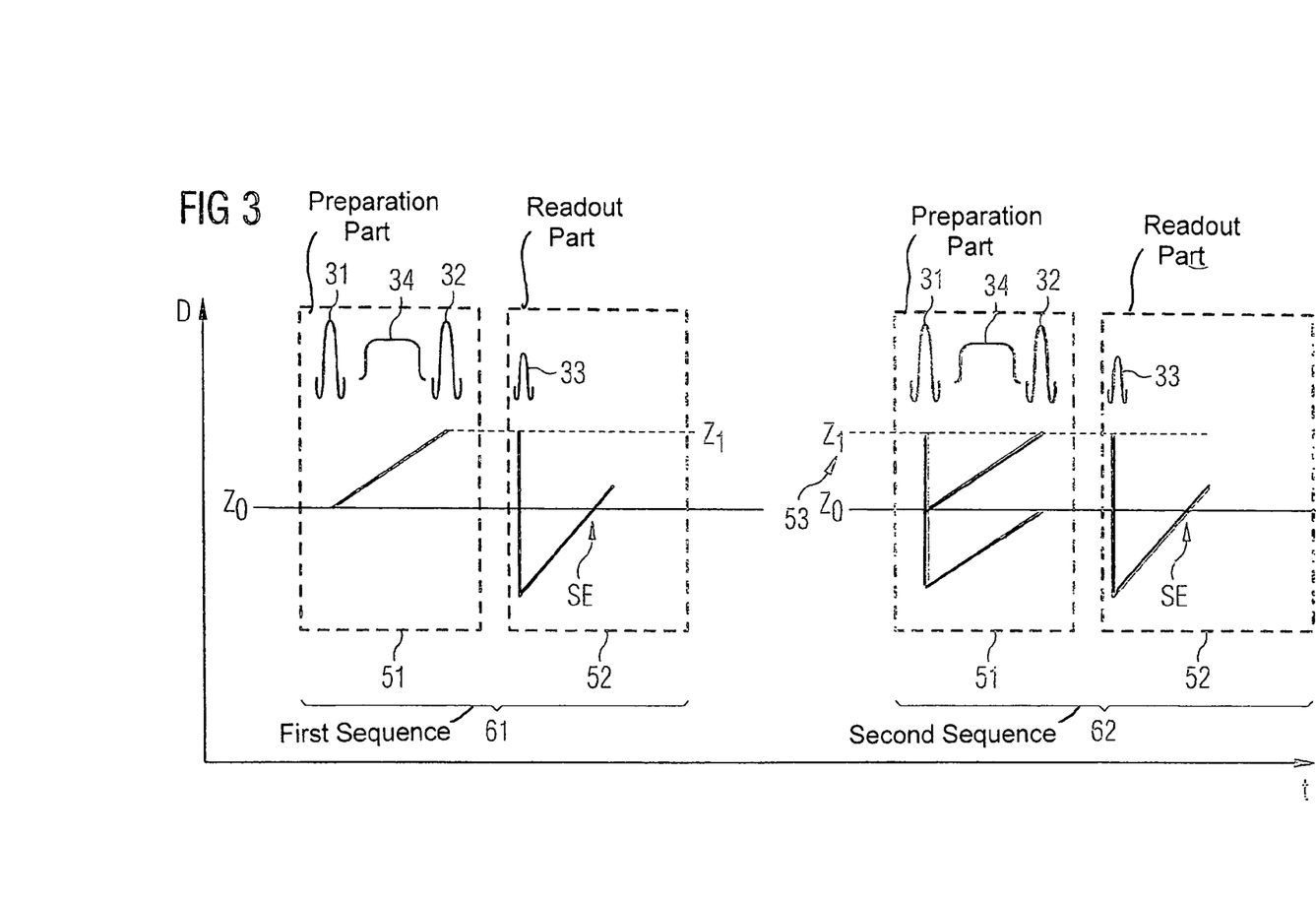
FIG. 3 shows various magnetization components that arise in first and second repetitions of a sequence according to the invention.

Defined magnetization components as well as their dephasing are schematically depicted in FIG. 3. $Z_0$ corresponds to the unprepared initial state or the originally present longitudinal component, and $Z_1$ corresponds to the longitudinal magnetic field component prepared by the preparation portion 51. Longitudinal magnetic field components which are not affected by the gradient are shown proceeding horizontally in FIG. 3. Transversal components travel diagonally in FIG. 3, whereby the dephasing influence of gradients is shown.

By the radiation of the first resonant RF pulse 31, a transverse component is generated which is subsequently dephased by the first gradient moment 41 and therefore is prepared. A defined proportion of the transversal component is flipped in the longitudinal direction or, respectively, converted into a longitudinal component $Z_1$ with the second resonant RF pulse 32. Since longitudinal components are not affected by gradient moments, the proportion of the transversal component that is flipped in the longitudinal direction is essentially stored by the radiation of the second RF pulse 32 until at least a defined portion of the longitudinal magnetization is converted by means of the third resonant RF pulse 33 into a transverse magnetization again. A stimulated echo SE is generated via the application of the second gradient moment 42 at a defined point in time and is read out upon readout of the MR data.

Via the radiation of the non-resonant RF pulse 34, a phase shift in the rotation movement of the nuclear spins is generated whose dimension is dependent on the strength of the actual B1 magnetic field (which is likewise generated by the radiated non-resonant RF pulse 34).

When, according to the invention, a second sequence 62 is now introduced chronologically immediately after the first sequence 61, the longitudinal component 53 prepared by the first sequence 61 has not yet decayed. If the flip angle or excitation angle of the first RF pulse 31 now deviates from 90°, a portion of the longitudinal magnetization component Z1 that is prepared in the first sequence remains. In this case the Z1 component present in the readout portion 52 of the second sequence 61 is composed of components prepared in different sequence executions (from the first sequence 61 and the second sequence 62 in the example) if the present invention were not used. The magnetization originating from the first sequence 61 is thereby designated with the reference character 53, which magnetization is at least partially converted into transverse and/or longitudinal components by the first and second resonant RF pulse 31, 32.

According to the invention, it is avoided that the stimulated echo is also formed by magnetization components of the first sequence 61 in the readout portion 52 of the second sequence 62, in that the first gradient moment 41 is selected differently in the first sequence 61 than in the second sequence 62 and/or in that the second gradient moment 42 is selected differently in the first sequence 61 than in the second sequence 62. In that the first gradient moment 41 and/or the second gradient moment 42 are/is selected differently in successive sequences 61, 62, it is ensured that only the echo of that longitudinal magnetization component which was also prepared in the preparation part 51 of the second sequence 62 is refocused at a specified point in time in the readout portion 52 of the second sequence 62. Longitudinal magnetization components of preceding sequences have different dephasings due to the different selection of the gradient moments 41, 42, such that only the stimulated echo SE which was also prepared by the current sequence 62 is advantageously detected in the readout of the MR data. An adulteration of the acquired MR data is therefore avoided, whereby an unadulterated phase can be measured in a determination of the B1 magnetic field according to the invention, and therefore a correct B1 magnetic field can be determined.

According to a preferred embodiment according to the invention, for this the same difference moment is added to or removed from the first gradient moment 41 of the second sequence 62 in comparison to the first gradient moment 41 of the first sequence 61 as is also added to or removed from the second gradient moment 42 of the second sequence 62 in comparison to the second gradient moment 42 of the first sequence 61. In other words: in this embodiment, both gradient moments or gradients 41, 42 are modified by the same difference moment from one sequence to the next following sequence.

Figure 4:
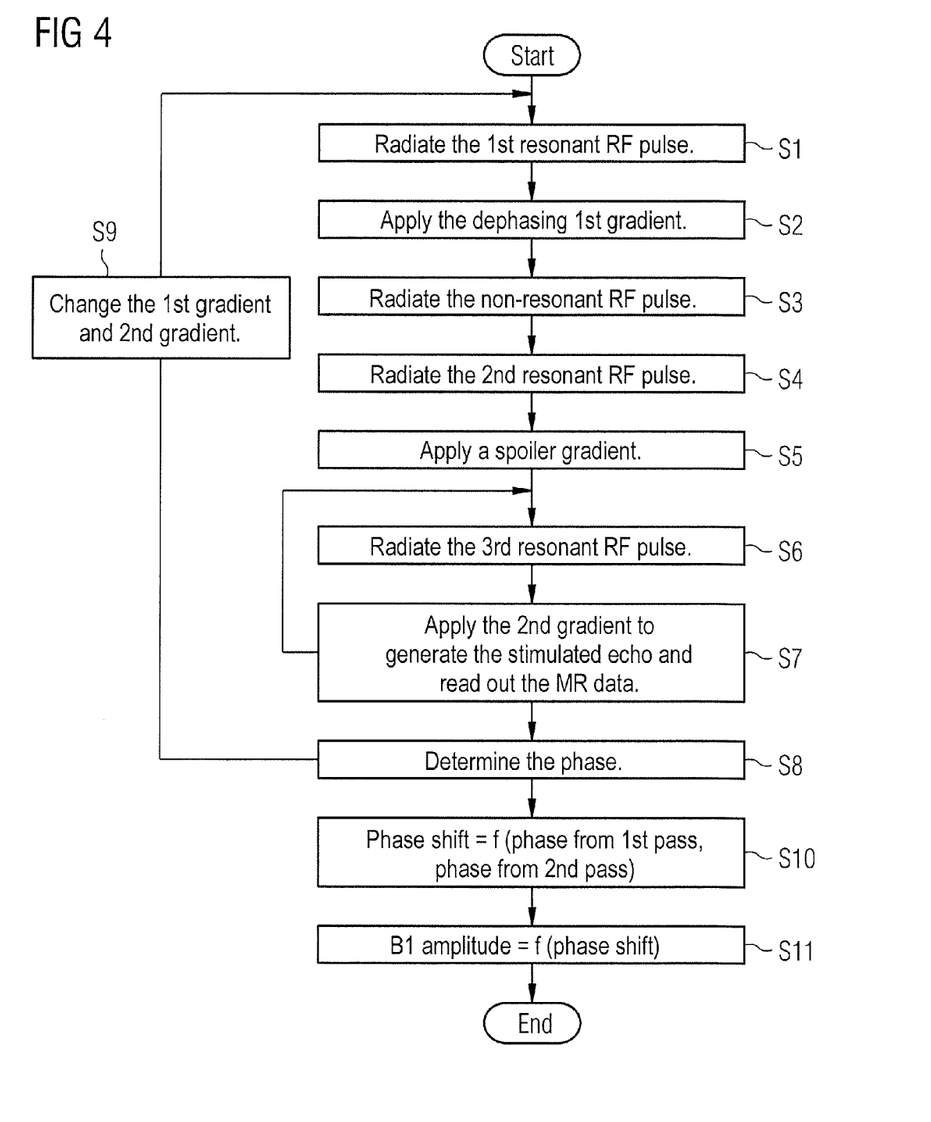
FIG. 4 is a flowchart of a method according to the invention to determine the B1 magnetic field.

A flowchart of a method according to the invention to determine the B1 magnetic field is presented in FIG. 4.

During a defined or arbitrary sequence, in a first Step S1 a first resonant RF pulse 31 is radiated, wherein a first dephasing gradient 41 is subsequently applied in a second Step S2. Before a second resonant RF pulse 32 is radiated in the fourth Step S4, in the third Step S3 a non-resonant RF pulse 34 is radiated which on the one hand generates the B1 magnetic field to be measured and on the other hand generates the phase shift. In order to destroy a transversal magnetization, in a fifth Step S5 a spoiler gradient 43 is applied. The Steps S1 through S5 belong to the preparation part 51 of the sequence 61, 62.

The readout portion 52 of the sequence 61, 62 begins with Step S6 of the radiation of a third resonant RF pulse 33. In Step S7, a second gradient 42 is subsequently applied in order to generate the stimulated echo SE which is detected upon readout of the MR data. Steps S6 and S7 are repeated arbitrarily often until the entirety of k-space has been read out, for example.

If the entirety of k-space has been registered, a phase value for arbitrary points within the volume segment can be determined using the acquired MR data. Since the phase shift depending on which the B1 magnetic field is determined can be calculated only from a difference of phase values, an additional sequence 62 is introduced directly following the defined sequence 61. That the first gradient 41 and the second gradient 42 generate different gradient moments in the additional sequence 62 than in the previous sequence 61 is indicated by Step S9. Steps S1 through S5 (the preparation part 51) are implemented again for the additional sequence 62, and in the subsequent readout part 52 Steps S6 and S7 are in turn repeated arbitrarily often until the entirety of k-space has been completely read out, for example.

After the implementation of the two sequences 61, 62, the phase shift can now be determined from the difference of the phase value from the determined sequence 61 and the phase value from the additional sequence 62 (see Step S10). In Step S11, the B1 amplitude for this location is calculated from the phase shift now calculated for an arbitrary location in the predetermined volume segment.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method to acquire magnetic resonance (MR) data from a volume segment of a subject situated in an MR data acquisition unit, comprising:

operating the MR data acquisition unit to repeatedly, in a plurality of repetitions, expose the subject situated in the MR data acquisition unit to an MR data acquisition sequence;

in each repetition of said sequence, operating the MR data acquisition unit to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

operating said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii); and in a processor, collecting all MR data read out in said plurality of repetitions in a data file, and making said data file available in electronic form at an output of the processor.

2. A method as claimed in claim 1 wherein said volume segment comprises a slice and, in each repetition of said sequence, applying a slice selection gradient during said first resonant RF pulse and during said second resonant RF pulse and during said third resonant RF pulse.

3. A method as claimed in claim 1 wherein said volume segment is a three-dimensional volume segment, and exciting nuclear spins in an entirety of said three-dimensional volume segment with each of said first resonant RF pulse, said second resonant RF pulse and said third resonant RF pulse.

4. A method as claimed in claim 1 comprising, in each repetition of said sequence, applying a spoiler gradient, that rephases transverse components of magnetization in the volume segment, after radiating said second resonant RF pulse and before radiating said third resonant RF pulse.

5. A method as claimed in claim 1 comprising radiating each of said first resonant RF pulse and said second resonant RF pulse with a flip angle of 90°.

6. A method as claimed in claim 1 comprising, in each repetition of said sequence, radiating said third resonant RF pulse, applying said second gradient, and reading out said MR data multiple times.

7. A method to determine a B1 magnetic field within a volume segment of a subject situated in a magnetic resonance (MR) data acquisition unit, comprising:

operating the MR data acquisition unit to repeatedly, in a plurality of repetitions, expose the subject situated in the MR data acquisition unit to an MR data acquisition sequence;

in each repetition of said sequence, operating the MR data acquisition unit to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

operating said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii);

operating said MR data acquisition unit to radiate a non-resonant RF pulse, after radiating said first resonant RF pulse and before radiating said second resonant RF pulse, in at least one of said respective repetition of said sequence and said next-successive repetition of said sequence, said non-resonant RF pulse producing a phase shift in said at least one repetition of said sequence in which said non-resonant RF pulse is radiated, relative to MR data read out in a repetition of said sequence in which said non-resonant RF pulse was not radiated;

in a processor, collecting all MR data read out in said plurality of repetitions in a data file and, in said processor, determining said phase shift from a difference of phase values of said MR data read out in said at least one of said sequences, and the phase values of MR data read out in said sequence in which said non-resonant RF pulse was not radiated;

in said processor, automatically determining an amplitude of a B1 magnetic field in said volume segment from said phase shift; and emitting an electronic signal from an output of said processor, which represents said amplitude of said B1 magnetic field.

8. A method as claimed in claim 7 comprising operating said MR data acquisition unit to radiate said non-resonant RF pulse in each of said respective repetition of said sequence and said next-successive repetition of said sequence, and comprising radiating said non-resonant RF pulse in said respective repetition of said sequence with a first frequency, and radiating said non-resonant RF pulse in said next-successive repetition of said sequence with a second frequency that differs from said first frequency.

9. A method as claimed in claim 8 wherein said MR data acquisition unit has a system frequency, and radiating the respective non-resonant RF pulses in said respective repetition of said sequence and in said next-successive repetition of said sequence with one of said first frequency and said second frequency being above said system frequency, and the other of said first frequency and said second frequency being below said system frequency.

10. A method as claimed in claim 7 comprising operating said MR data acquisition unit to repeat said sequence three times, so that said plurality of repetitions consist of a first repetition, a second repetition and a third repetition;

operating said MR data acquisition unit to radiate said non-resonant RF pulse in each of said second repetition and said third repetition; and operating said MR data acquisition unit to radiate said non-resonant RF pulse in said second repetition with a frequency that differs from a frequency of the non-resonant RF pulse radiated in said third repetition.

11. A method as claimed in claim 10 wherein said MR data acquisition unit comprises multiple transmission channels, and comprising:

radiating said non-resonant RF pulse in each of said respective repetition of said sequence and said next-successive repetition of said sequence, via a same set of said transmission channels, comprising at least one of said transmission channels, in both said respective repetition of said sequence and said next-successive repetition of said sequence; and in said processor, determining the B1 magnetic field in said volume segment as a B1 magnetic field generated in said volume segment by said set of transmission channels.

12. A magnetic resonance (MR) apparatus comprising:

an MR data acquisition unit comprising at least one radio frequency (RF) antenna, at least one reception coil element, a gradient field system and a control unit, said MR data acquisition unit being configured to receive a subject therein comprising a volume segment;

a control unit configured to operate the MR data acquisition unit to repeatedly, in a plurality of repetitions, expose the subject situated in the MR data acquisition unit to an MR data acquisition sequence;

said control unit being configured to operate the MR data acquisition unit in each repetition of said sequence, to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

said control unit being configured to operate said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii); and a processor configured to collect all MR data read out in said plurality of repetitions in a data file, and to make said data file available in electronic form at an output of the processor.

13. A magnetic resonance apparatus comprising:

an MR data acquisition unit comprising at least one radio frequency (RF) antenna, at least one reception coil element, a gradient field system and a control unit, said MR data acquisition unit being configured to receive a subject therein comprising a volume segment;

a control unit configured to operate the MR data acquisition unit to repeatedly, in a plurality of repetitions, expose the subject situated in the MR data acquisition unit to an MR data acquisition sequence;

said control unit being configured to operate the MR data acquisition unit in each repetition of said sequence, to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

said control unit being configured to operate said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii);

operating said MR data acquisition unit to radiate a non-resonant RF pulse, after radiating said first resonant RF pulse and before radiating said second resonant RF pulse, in at least one of said respective repetition of said sequence and said next-successive repetition of said sequence, said non-resonant RF pulse producing a phase shift in said at least one repetition of said sequence in which said non-resonant RF pulse is radiated, relative to MR data read out in a repetition of said sequence in which said non-resonant RF pulse was not radiated;

in a processor, collecting all MR data read out in said plurality of repetitions in a data file and, in said processor, determining said phase shift from a difference of phase values of said MR data read out in said at least one of said sequences, and the phase values of MR data read out in said sequence in which said non-resonant RF pulse was not radiated;

in said processor, automatically determining an amplitude of a B1 magnetic field in said volume segment from said phase shift; and emitting an electronic signal from an output of said processor, which represents said amplitude of said B1 magnetic field.

14. A non-transitory, computer-readable data storage medium encoded with programming instructions, said data storage medium being loaded into a computerized control and processing system of a magnetic resonance (MR) apparatus, said MR apparatus comprising an MR data acquisition unit in which a subject, comprising a volume segment, is situated, said programming instructions causing said control and processing system to:

operate the MR data acquisition unit to repeatedly, in a plurality of repetitions, expose the subject situated in the MR data acquisition unit to an MR data acquisition sequence;

in each repetition of said sequence, operate the MR data acquisition unit to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

operate said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii); and collect all MR data read out in said plurality of repetitions in a data file, and make said data file available in electronic form at an output of the processing system.

15. A non-transitory, computer-readable data storage medium encoded with programming instructions, said data storage medium being loaded into a computerized control and processing system of a magnetic resonance (MR) apparatus, said MR apparatus comprising an MR data acquisition unit in which a subject, comprising a volume segment, is situated, said programming instructions causing said control and processing system to:

operate the MR data acquisition unit to repeatedly, in a plurality of repetitions, expose the subject situated in the MR data acquisition unit to an MR data acquisition sequence;

in each repetition of said sequence, operate the MR data acquisition unit to radiate a first resonant radio-frequency (RF) pulse, radiate a second resonant RF pulse after radiating said first resonant RF pulse, apply a dephasing first gradient after radiating the first resonant RF pulse and before radiating the second resonant RF pulse, radiate a third resonant RF pulse after radiating the second resonant RF pulse, apply a second gradient after radiating the third RF resonant pulse, that refocuses a stimulated echo of a magnetization component in the subject prepared by the dephasing first gradient, and reading out MR data associated with the stimulated echo;

operate said MR data acquisition unit with a dissimilarity between a respective repetition, among said plurality of repetitions, and a next-successive repetition that directly follows said respective repetition, said dissimilarity being selected from the group consisting of (i) said first gradient in said respective repetition differing from said first gradient in said next-successive repetition, (ii) said second gradient in said respective repetition differing from said second gradient in said next-successive repetition, and (iii) both (i) and (ii);

operating said MR data acquisition unit to radiate a non-resonant RF pulse, after radiating said first resonant RF pulse and before radiating said second resonant RF pulse, in at least one of said respective repetition of said sequence and said next-successive repetition of said sequence, said non-resonant RF pulse producing a phase shift in said at least one repetition of said sequence in which said non-resonant RF pulse is radiated, relative to MR data read out in a repetition of said sequence in which said non-resonant RF pulse was not radiated;

collect all MR data read out in said plurality of repetitions in a data file, and determine said phase shift from a difference of phase values of said MR data read out in said at least one of said sequences, and the phase values of MR data read out in said sequence in which said non-resonant RF pulse was not radiated;

automatically determine an amplitude of a B1 magnetic field in said volume segment from said phase shift; and an electronic signal from an output of said processing system, which represents said amplitude of said B1 magnetic field.

* * * * *